United States Patent [19]
Matsumoto et al.

[11] Patent Number: 5,922,659
[45] Date of Patent: Jul. 13, 1999

[54] CLEANSER COMPOSITION

[75] Inventors: Chikako Matsumoto; Tadashi Moriyama, both of Wakayama; Takatoshi Kobayashi, Tochigi; Yuichi Hioki, Wakayama; Takashi Imamura, Osaka, all of Japan

[73] Assignee: Kao Corporation, Tokyo, Japan

[21] Appl. No.: 08/789,536

[22] Filed: Jan. 27, 1997

Related U.S. Application Data

[63] Continuation of application No. 08/436,303, filed as application No. PCT/JP94/01566, Sep. 22, 1994., abandoned

[30]  Foreign Application Priority Data

Sep. 24, 1993 [JP] Japan ................................. 5-238159

[51] Int. Cl.$^6$ .............................. C11D 1/02; C11D 3/26; C11D 3/32
[52] U.S. Cl. .................... 510/126; 510/123; 510/124; 510/137; 510/138; 510/158; 510/159; 510/501
[58] Field of Search .................... 510/124, 123, 510/126, 137, 138, 158, 159, 501

[56]  References Cited

U.S. PATENT DOCUMENTS

| | | | |
|---|---|---|---|
| 4,479,893 | 10/1984 | Hirota et al. | 252/542 |
| 4,758,376 | 7/1988 | Hirota et al. | 252/545 |
| 4,783,282 | 11/1988 | Smid | 252/546 |
| 4,818,440 | 4/1989 | Schäfer et al. | 252/546 |

FOREIGN PATENT DOCUMENTS

| | | |
|---|---|---|
| 0102118 | 3/1984 | European Pat. Off. . |
| 219893 | 1/1989 | European Pat. Off. . |
| 138593 | 6/1987 | Japan . |
| 240390 | 10/1987 | Japan . |

OTHER PUBLICATIONS

English language abstract of EP–A–102118.
English language abstract of JP–A–62–240390.
English language abstract of JP–A–62–138593.
English language abstract EP–219893.

*Primary Examiner*—Margaret Einsmann
*Assistant Examiner*—Gregory R. Delcotto
*Attorney, Agent, or Firm*—Birch, Stewart, Kolasch & Birch, LLP

[57]  ABSTRACT

A cleanser composition comprising a phosphate type surfactant and an amide ether carboxylic acid as the essential components. This cleanser composition is lowly irritant to the skin etc., and excellent in lathering property, gives creamy foam in quality, and can give an excellent feeling to the skin cleansed even when it is used in hard water.

10 Claims, No Drawings

CLEANSER COMPOSITION

This application is a continuation, of application Ser. No. 08/436,303 filed on May 19, 1995, now abandoned, which is a 371 of PCT/JP094/01566 filed Sep. 22, 1994.

FIELD OF THE INVENTION

The present invention relates to a cleanser composition, more particular a cleanser composition which is lowly irritant to the skin etc., and excellent in lathering property, gives creamy foam in quality, and can give an excellent feeling to the skin cleansed even when it is used in hard water.

DESCRIPTION OF THE RELATED ART

As surfactants for cleansers, anionic surfactants such as salts of alkyl sulfates, salts of polyoxyethylene alkyl sulfates, alkylbenzenesulfonates and α-olefinsulfonates, which are characterized in their high lathering property, have hitherto been used widely. However, these anionic surfactants have a disadvantage that every anionic surfactant is irritant to the skin to chap the skin when used repeatedly, though the extent of its irritation varies.

In contrast, phosphate type surfactants comprising monoalkylphosphoric acid as the main component have a problem that when they are used in hard water, calcium salts of phosphoric acid eaters are formed and remain on the skin even after rinsing to give somewhat dry feeling to the skin, though they are lowly irritant and excellent in lathering property and foam quality thereof.

Alkylsaccharide type surfactants, sulfosuccinic acid type surfactants, ether carboxylic acid type surfactants and amide ether carboxylic acid type surfactants are also known as lowly irritant surfactants. Alkylsaccharide type surfactants squeak in cleansing and rinsing, though they have a high lathering property. Therefore, the simultaneous use of an alkylsaccharide type surfactant with a conditioning agent such as a cationic polymer has been proposed. However, it is technically difficult to incorporate such a conditioning agent to a shampoo or the like in a large amount. Sulfosuccinic acid type surfactants are poor in lathering property each by itself, so that the simultaneous use thereof with other surfactant has been proposed. In practical use thereof, a sulfosuccinic acid type surfactant is generally used together with other surfactant. Commercially available ether carboxylic acid type and amide ether carboxylic acid type surfactants are also poor in lathering property, so that they are used merely as an auxiliary surfactant in the fields requiring a high lathering property.

Among the above lowly irritant surfactants, an amide ether carboxylic acid type surfactant is commercially available under the tradename of Akypo from Chem-Y GmbH, Germany. The Akypo contains polyoxyethylene glyceryl ether, polyoxyethylene glyceryl ether carboxylic acid, inorganic salts and so forth which are impurities originated from its raw material, in addition to an amide ether carboxylic acid and an amide ether which is the raw material thereof.

Known techniques for the application of the amide ether carboxylic acid type surfactants to cleanser compositions include a cleanser composition comprising an amide ether carboxylic acid and, combined therewith, a polyoxyethylene alkyl sulfate, a diethanolamide of a fatty acid, an alkylene oxide adduct of a higher alcohol, an acylsarcosinate or the like (European Patent Publication-A No. 102118, published on Mar. 7, 1984), a process of using an amide ether carboxylic acid type surfactant together with a polyoxyethylene alkyl sulfate, a cleanser for foam bath, shampoo, showering or the like which comprises an amide ether carboxylic acid prepared from a fat or oil as the raw material, and, combined therewith, a quaternary compound prepared by reacting glycidyltrimethylammonium chloride with lauryl sulfate, lauryl ether sulfate, alkyl ether carboxylic acid or lauric acid, a cleanser composition comprising a soap as the main component, and further an amide ether carboxylic acid and an alkyl ether carboxylic acid salt and others. However, these cleansers are still unsatisfactory in lathering property.

Accordingly, an object of the present invention is to provide a cleanser composition which is lowly irritant to the skin etc., exhibits a high lathering property, gives creamy foam in quality, and can give an excellent feeling to the skin cleansed even when it is used in hard water.

DISCLOSURE OF THE INVENTION

Under these circumstances, the present inventors have extensively studied to solve the above problems. As the result, they have found that a cleanser composition comprising a phosphate type surfactant and an amide ether carboxylic acid is lowly irritant to the skin etc, exhibits a high lathering property, gives creamy foam in quality, and is excellent in feeling to the skin cleansed even when it is used in hard water, and that the lathering property and the quality of foam can be further improved by using also an amide ether together with the above components. The present invention has been accomplished on the basis of these findings.

Thus, the present invention provides a cleanser composition comprising the following components (A) and (B):

component (A): a phosphate type surfactant (1) represented by the following formula (1), or a mixture of the phosphate type surfactant (1) and a phosphate type surfactant (2) represented by the following formula (2), wherein the weight ratio of the phosphate type surfactant (1) to the phosphate type surfactant (2) is from 100/0 to 70/30;

wherein $R^1$ represents a linear or branched alkyl or alkenyl group having 6 to 24 carbon atoms, and $X^1$ and Y each represents a hydrogen atom, an alkali metal atom, ½(alkaline earth metal atom), an ammonium group, an alkanolammonium group or a group consisting of one hydrogen atom and a basic amino acid, and

wherein $R^2$ and $R^3$ each represents a linear or branched alkyl or alkenyl group having 6 to 24 carbon atoms, and $X^2$ represents a hydrogen atom, an alkali metal atom, ½(alkaline earth metal atom), an ammonium group, an alkanolammonium group or a group consisting of one hydrogen atom and a basic amino acid; and component (B): at least one amide ether carboxylic acid (3) selected from the group consisting of amide ether carboxylic acids represented by the following formula (3-1) and amide ether carboxylic acids represented by the following formula (3-2), or a mixture of the amide ether carboxylic acid (3) and at least one amide ether (4) selected from the group consisting of amide ethers represented by the following formula (4-1) and amide ethers represented by the following formula (4-2), wherein the weight ratio of the amide ether carboxylic acid (3) to the amide ether (4) is from 100/0 to 10/90;

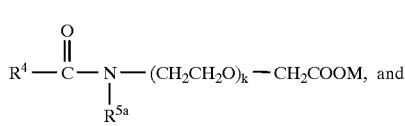  (3-1)

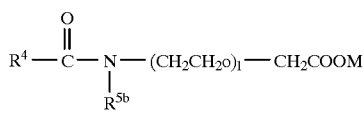  (3-2)

wherein M represents a hydrogen atom, an alkali metal atom, ½(alkaline earth metal atom), an ammonium group, an alkanolammonium group or a group consisting of one hydrogen atom and a basic amino acid, $R^4$ represents a linear or branched alkyl or alkenyl group having 5 to 23 carbon atoms or a phenyl group which may be substituted with a linear or branched alkyl or alkenyl group having 5 to 23 carbon atoms, $R^{5a}$ represents a hydrogen atom or an alkyl group having 1 to 3 carbon atoms, $R^{5b}$ represents —$(CH_2CH_2O)_m$—$CH_2COOM$, wherein M is as defined above, or —$(CH_2CH_2O)_n$—H, k is a number of 1 to 20, l, m and n are each a number of 1 or more, and, wherein x and y are each a number of 0 to 1 and satisfy the relationship of x+y=1, is a number of 2 to 20, and

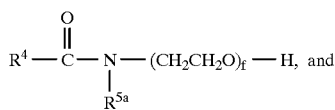  (4-1)

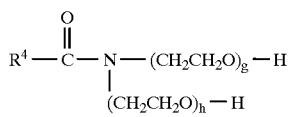  (4-2)

wherein $R^4$ and $R^{5a}$ are each as defined above, q-a is a number of 1 to 20, g and h are each a number of 1 or more; and g-h, is a number of 2 to 20.

The cleanser composition of the present invention may further comprise a glycerol derivative (5) represented by the following formula (5) in an amount of at most 5% by weight based on the sum total weight of the component (B) and the glycerol derivative (5):

wherein $R^6$ represents —$(CH_2CH_2O)_{r-1}$—$CH_2COOM$, wherein M is as defined above, or —$(CH_2CH_2O)_{s-1}$H, $R^7$ represents —$(CH_2CH_2O)_{r-2}$—$CH_2COOM$, wherein M is as defined above, or —$(CH_2CH_2O)_{s-2}$—H, $R^8$ represents —$(CH_2CH_2O)_{r-3}$—$CH_2COOM$, wherein M is as defined above, or —$(CH_2CH_2O)_{s-3}$—H, r-1, s-1, r-2, s-2, r-3 and s-3 are each 0 or a positive number and z, which is defined as $\{x_1(r-1)+y_1(s-1)\}+\{x_2(r-2)+y_2(s-2)\}+\{x_3(r-3)+y_3(s-3)\}$, wherein $x_1$ and $y_1$ are each a number of 0 to 1 and satisfying the relationship of $x_1+y_1=1$, $x_2$ and $y_2$ are each a number of 0 to 1 and satisfying the relationship of $x_2+y_2=1$, and $x_3$ and $y_3$ are each a number of 0 to 1 and satisfying the relationship of $x_3+y_3=1$, is a number of 0 to 57.

Further, the present invention includes a cleanser composition, wherein the component (A) is as defined above wherein $R^1$, $R^2$ and $R^3$ each represents a linear or branched alkyl or alkenyl group having 8 to 18 carbon atoms, and $X^1$, $X^2$ and Y each represents a hydrogen atom, an alkali metal atom, a triethanol-ammonium group or an ammonium group, and the component (B) consists of an amide ether carboxylic acid represented by the formula (3-1) wherein $R^4$ represents a linear or branched alkyl or alkenyl group having 8 to 18 carbon atoms, $R^{5a}$ represents a hydrogen atom, M represents a hydrogen atom, an alkali metal atom, a triethanolammonium group or an ammonium group, and K is a number of 3 to 15.

In other words, the present invention includes a cleanser composition comprising the following components (A') and (B') as the essential components:

component (A'): a phosphate type surfactant comprising a phosphate type surfactant represented by the following formula (1') or a mixture thereof with another phosphate type surfactant represented by the following formula (2'), wherein the weight ratio between them comprised is (1')/(2') of from 100/0 to 70/30;

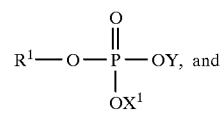  (1')

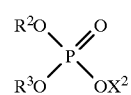  (2')

wherein $R^1$, $R^2$ and $R^3$ each represents a linear or branched alkyl or alkenyl group having 8 to 18 carbon atoms, and $X^1$, $X^2$ and Y each represents a hydrogen atom, an alkali metal atom, triethanolamine or ammonium, and component (B'): an ether acetic acid type surfactant represented by the following formula (3')

$$R^4\text{—CONH—}(CH_2CH_2O)_p\text{—}CH_2COOM \quad (3')$$

wherein $R^4$ represents a linear or branched alkyl or alkenyl group having 8 to 18 carbon atoms, M represents a hydrogen atom, an alkali metal atom, triethanolamine or ammonium, and p is a number of 3 to 15.

Among the cleanser compositions comprising the above components (A') and (B') as the essential components, those wherein $X^1$, $X^2$, Y and M each represents an alkali metal atom are preferable.

In the present invention, the phosphate type surfactants to be used as the component (A) are represented by the formulas (1) and (2).

Although $R^1$ in the formula (1) and $R^2$ and $R^3$ in the formula (2) each represents a linear or branched alkyl or alkenyl group having 6 to 24 carbon atoms, those each having 8 to 18 carbon atoms are preferred, those each having 12 to 14 carbon atoms are still more preferred and alkyl groups each having 12 to 14 carbon atoms are particularly preferred.

Examples of the above alkyl or alkenyl group include octyl group, nonyl group, decyl group, undecyl group, dodecyl group, tridecyl group, tetradecyl group, pentadecyl group, heptadecyl group and octadecyl group.

$X^1$ and Y in the formula (1) and $X^2$ in the formula (2) each represents a hydrogen atom, an alkali metal atom, ½(alkaline earth metal atom) such as ½$Ca^{2+}$, an ammonium group, an alkanolammonium group or a group consisting of one hydrogen atom and a basic amino acid.

Examples of the alkali metal atom include sodium atom and potassium atom; those of the alkaline earth metal atom include magnesium atom and calcium atom; those of the alkanolammonium group include monoethanolammonium group, diethanolammonium group and triethanolammonium group; and those of the amino acid constituting the group consisting of one hydrogen atom and a basic amino acid include arginine and lysine. Among them, alkali metal atoms and triethanolammonium group are preferable, and potassium atom is particularly preferred from the standpoint of solubility in water.

The component (A) contains a phosphate type surfactant represented by the formula (1) (hereinafter referred to as the monoalkyl phosphate (1)) in an amount of at least 70% by weight, preferably at least 80% by weight based on the sum total of the monoalkyl phosphate (1) and another phosphate type surfactant represented by the formula (2) (hereinafter referred to as the dialkyl phosphate (2)). When the monoalkyl phosphate (1) is less than 70% by weight, the lathering property and detergency of the cleanser composition to be obtained are poor, unfavorably.

The cleanser composition of the present invention contains the component (A) in an amount of generally 0.5 to 40% by weight, preferably 1 to 20% by weight, still more preferably 3 to 15% by weight based on the total weight of the composition. When the amount of the component (A) is too small, the resulting cleanser composition will be unsufficient in lathering property and quality of foam (creaminess).

Those to be used as the component (B) in the present invention are at least one amide ether carboxylic acid (3) selected from the group consisting of those represented by the formula (3-1) and those represented by the formula (3-2) and at least one amide ether (4) selected from the group consisting of those represented by the formula (4-1) and those represented by the formula (4-2).

Although $R^4$ in the formulae (3-1), (3-2), (4-1) and (4-2) represents a linear or branched alkyl or alkenyl group having 5 to 23 carbon atoms or a phenyl group which may be substituted with a linear or branched alkyl or alkenyl group having 5 to 23 carbon atoms, alkyl or alkenyl groups each having 7 to 17 carbon atoms, such as heptyl group, nonyl group, undecyl group, tridecyl group, pentadecyl group, heptadecyl group and heptadecenyl group, and phenyl groups each substituted with such an alkyl or alkenyl group are preferable, and alkyl groups each having 11 to 13 carbon atoms are particularly preferable.

The amide ether carboxylic acid (3) is preferably one represented by the formula (3-1). In the formula (3-1), $R^{5a}$ is a hydrogen atom or an alkyl group having 1 to 3 carbon atoms. p-a in the formula (3-1) represents the average number of oxyethylene groups. When an amide ether carboxylic acid represented by the formula (3-1) is prepared from monoethanolamide as will be described below, k represents the average number of ethylene oxides added plus 1. k is desirably 1 to 15, still more desirably 1 to 10, particularly desirably 2 to 7.

Specific examples of M in the formula (3-1) include those the same as the specific examples of $X^1$, $X^2$ and Y described above.

In the formula (3-2), $R^{5b}$ represents —$(CH_2CH_2O)_m$—$CH_2COOM$, wherein M is as defined above, or —$(CH_2CH_2O)_n$—H.

l, m and n are each a number of 1 or above; and p-b, which is defined as $(1)+\{x(m)+y(n)\}$, wherein x and y are each a number of 0 to 1 and satisfying the relationship of x+y=1, is a number of 2 to 20, That is, when the amide ether carboxylic acid is

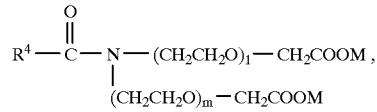

while when it is represented by the formula:

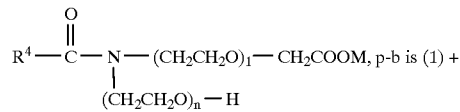

p-b is (p-1)+(n).

Further, when the amide ether carboxylic acid is a mixture of those represented by these two formulae respectively, p-b is $(1)+\{x(m)+y(n)\}$.

p-b in the formula (3-2) represents the average number of oxyethylene groups contained in one molecule. When an amide ether carboxylic acid represented by the formula (3-2) is prepared from diethanolamide as will be described below, p-b represents the average number of ethylene oxides added plus 2. p-b is desirably 2 to 15, still more desirably 2 to 10, particularly desirably 2 to 7.

Specific examples of M in the formula (3-2) include those the same as the specific examples of $X^1$, $X^2$ and Y described above listed above.

The amide ether (4) is preferably one represented by the formula (4-1). In the formula (4-1), $R^{5a}$ is a hydrogen atom or an alkyl group having 1 to 3 carbon atoms. f in the formula (4-1) represents the average number of oxyethylene groups. When an amide ether represented by the formula (4-1) is prepared from monoethanolamide as will be described below, f represents the average number of ethylene oxides added plus 1. f is desirably 1 to 15, still more desirably 1 to 10, particularly desirably 2 to 7.

In the formula (4-2), g and h are each a number of 1 or above, while q-b, which is defined as (g)+(h), is a number of 2 to 20.

q-b in the formula (4-2) represents the average number of oxyethylene groups contained in one molecule. When an amide ether represented by the formula (4-2) is prepared from diethanolamide as will be described below, q-b represents (the average number of ethylene oxides added plus 2). q-b is desirably 2 to 15, still more desirably 2 to 10, particularly desirably 2 to 7.

Desirable and specific examples of the amide ether carboxylic acid (3) include capric monoethanolamide polyoxyethylene ether acetic acid, i.e., mono-(capramidopolyoxyethylene)acetic acid (k=1 to 15), lauric monoethanolamide polyoxyethylene ether acetic acid (k=1 to 15), myristic monoethanolamide polyoxyethylene ether acetic acid (k=1 to 15), palmitic monoethanolamide polyoxyethylene ether acetic acid (k=1 to 15), stearic monoethanolamide polyoxyethylene ether acetic acid (k=1 to 15), oleic monoethanolamide polyoxyethylene ether acetic acid (k=1 to 20), behenic monoethanolamide polyoxyethylene ether acetic acid (k=1 to 20), lauric N-methylethanolamide polyoxyethylene ether acetic acid, i.e., mono(N-methyllauramidopolyoxy-ethylene)acetic acid (k=1 to 15)], myristic N-methylethanolamide polyoxyethylene ether acetic acid (k=1 to 15), palmitic N-methylethanolamide polyoxyethylene ether acetic acid (k=1 to 15), stearic N-methylethanol amide polyoxyethylene ether acetic acid (k=1 to 15), lauric diethanolamide polyoxyethylene ether acetic acid, i.e., lauramido-N,N-di(polyoxyethyleneacetic acid) (p-b=2 to 15)], myristic diethanolamide polyoxyethylene ether acetic acid (p-b=2 to 15), palmitic diethanolamide polyoxyethylene ether acetic acid (p-b=2 to 15), stearic diethanolamide polyoxyethylene ether acetic acid (p-b=2 to 15), and salts thereof. Still more desirable and specific examples thereof include lauric monoethanolamide polyoxyethylene ether acetic acid (k=1 to 10), myristic monoethanolamide polyoxyethylene ether acetic acid (k=1 to 10), palmitic monoethanolamide polyoxyethylene ether acetic acid (k=1 to 10), stearic monoethanolamide polyoxyethylene ether acetic acid (k=1 to 10), and salts thereof. Particularly desirable and specific examples thereof include lauric monoethanolamide polyoxyethylene ether acetic acid (k=2 to 7), myristic monoethanolamide polyoxyethylene ether acetic acid (k=2 to 7), and salts thereof.

Desirable and specific examples of the amide ether (4) include capric monoethanolamide polyoxyethylene ether, i.e., capramidopolyoxyethylene ether (f=1 to 15), lauric monoethanolamide polyoxyethylene ether (f=1 to 15), myristic monoethanolamide polyoxyethylene ether (f=1 to 15), palmitic monoethanolamide polyoxyethylene ether (f=1 to 15), stearic mbnoethanolamide polyoxyethylene ether (f=1 to 15), oleic monoethanolamide polyoxyethylene ether (f=1 to 20), behenic monoethanolamide polyoxyethylene ether (f=1 to 20), lauric N-methylethanolamide polyoxyethylene ether, i.e. N-methyllauramidopolyoxyethylene ether (f=1 to 15), myristic N-methylethanolamide polyoxyethylene ether (f=1 to 15), palmitic N-methylethanolamide polyoxyethylene ether (f=1 to 15), stearic N-methylethanolamide polyoxyethylene ether (f=1 to 15), lauric diethanolamide polyoxyethylene ether, i.e., lauramido-N,N-di(polyoxyethylene ether) (q-b=2 to 15), myristic diethanolamide polyoxyethylene ether (q-b=2 to 15), palmitic diethanolamide polyoxyethylene ether (q-b=2 to 15) and stearic diethanolamide polyoxyethylene ether (q-b=2 to 15). Still more desirable and specific examples thereof include lauric monoethanolamide polyoxyethylene ether (f=1 to 10), myristic monoethanolamide polyoxyethylene ether (f=1 to 10), palmitic monoethanolamide polyoxyethylene ether (f=1 to 10), and stearic monoethanolamide polyoxyethylene ether (f=1 to 10). Particularly desirable and specific examples thereof include lauric monoethanolamide polyoxyethylene ether (f=2 to 7) and myristic monoethanolamide polyoxyethylene ether (f=2 to 7).

Although the component (B) is an amide ether carboxylic acid (3) alone or a mixture thereof with an amide ether (4), the mixture is preferable.

Although the weight ratio of the amide ether carboxylic acid (3) to the amide ether (4), i.e., (3)/(4), in the component (B), is from 100/0 to 10/90, it is desirably from 99/1 to 10/90, still more desirably from 95/5 to 60/40, particularly desirably from 92/8 to 70/30. When the proportion of the amide ether (4) is too low, the cleanser composition to be obtained will be poor in lathering property, while when it is too high, it will strongly squeak in lathering and rinsing, unfavorably.

The amide ether carboxylic acid (3) to be used in the present invention as the component (B) can be prepared by, e.g., the process described in European Patent No. 219893. Meanwhile, the mixture of the amide ether carboxylic acid (3) with the amide ether (4) to be used as the component (B) (hereinafter sometimes referred to as amide ether derivative mixture) can be prepared by, e.g., reacting part of the amide ether (4) with a halogenoacetic acid directly or adding the amide ether (4) to the amide ether carboxylic acid (3).

Examples of the process for preparing the amide ether (4) which is the intermediate for the preparation of the amide ether carboxylic acid (3) include a process which comprises using a lower alkyl ester of a fatty acid, such as methyl ester of a fatty acid, as the starting material, reacting it with an alkanolamine and adding ethylene oxide thereto, a process which comprises using a fat or oil as the starting material, reacting it with an alkanolamine and adding ethylene oxide thereto, and a process which comprises using a fatty acid as the starting material, reacting it with an alkanolamine and adding ethylene oxide thereto. Among these processes, the process using a lower alkyl ester of a fatty acid, such as methyl ester of a fatty acid, as the starting material is preferable, because the product thereof is little discolored and is substantially free from glycerol derivative (5) as impurities.

The employment of other process, for example, a process which comprises using coconut oil as the starting material, reacting it directly with an alkanolamine and adding ethylene oxide thereto, is unfavorable, because glycerol derivative (5) originating from the fat or oil are formed in a large amount to lower the yield of the amide ether (4), which results in a lowered yield of the amide ether carboxylic acid (3).

Further, the process which comprises using a fatty acid as the starting material and reacting it with an alkanolamine is also unfavorable, because the amidation must be conducted at high temperature to cause a remarkable discoloration.

When the amide ether derivative mixture to be used as the component (B) is directly prepared, the ratio between the amide ether carboxylic acid (3) and the amide ether (4) can be controlled by selecting the reaction conditions employed in reacting the amide ether (4) with an alkali metal salt of monohalogenoacetic acid or the like, for example, the molar ratio thereof and the means of mixing.

In the production of the component (B), as described above, the reaction product may contain the above glycerol derivative (5) owing to its production process. The cleanser composition of the present invention also includes those prepared with the use of such a reaction product containing the glycerol derivative (5) in an amount of 5% by weight or below based on the sum total weight of the component (B)

and the glycerol derivative (5) or the one containing the glycerol derivative (5) in an amount of 5% by weight or below based on the solid content (weight) of the reaction product.

The above formula (5) will now be described.

First, $R^6$ in the formula (5) will be described.

When $x_1$ is 1 and $y_1$ is 0, $R^6$ is represented by —$(CH_2CH_2O)_{r-1}$—$CH_2COOM$, and when r-1 is 0 in addition to them, $R^6$ is represented by —$CH_2COOM$. On the other hand, when $x_1$ is 0 and $y_1$ is 1, $R^6$ is represented by —$(CH_2CH_2O)_{s-1}$—H, and when s-1 is 0 in addition to them, $R^6$ represents a hydrogen atom. When a group represented by —$(CH_2CH_2O)_{r-1}$—$CH_2COOM$ and one represented by —$(CH_2CH_2O)_{s-1}$—H are present in a mixed state as $R^6$, in other words, when the glycerol derivative (5) is a mixture of a compound wherein $R^6$ is —$(CH_2CH_2O)_{r-1}$—$CH_2COOM$ and another compound wherein $R^6$ is —$(CH_2CH_2O)_{s-1}$—H, $x_1$ and $y_1$, each represents a number exceeding 0 but below 1, with the proviso that they satisfy the relationship of $x_1+y_1=1$. $R^7$ and $R^8$ are the same as defined above with respect to $R^6$.

Further, the addition of ethylene oxide occurs at ramdom, so that r-1, s-1, r-2, s-2, r-3 and s-3 in the formula (5) are not respectively specified, but z, which is defined as $\{x_1(r-1)+y_1(s-1)\}+\{x_2(r-2)+y_2(s-2)\}+\{x_3(r-3)+y_3(s-3)\}$ and represents the average number of ethylene oxides added per molecule of the glycerol derivative (5), must be a number of 0 to 57.

In the present invention, the cleanser composition of the present invention may be also prepared with the use of a solution containing the component (B), for example, the reaction product mixture. As such a solution used in the present invention, those wherein the sum total of the amide ether carboxylic acid (3) and the amide ether (4) is at least 50% by weight based on the solid content (weight) of the solution are preferable, those wherein the sum total thereof is at least 60% by weight are still more preferable, those wherein the sum total thereof is at least 70% by weight are particularly preferable, and those wherein the sum total thereof is at least 80% by weight are most preferable. The term "solid content" refers to the value found by subtracting the water content (%) of the above solution as determined by the Karl Fischer method from 100%.

Meanwhile, when the above solution containing the component (B) is one containing also the above glycerol derivative (5), those wherein the content of the derivative (5) is 5% by weight or below based on the sum total weight of the component (B) and the glycerol derivative (5) can be used for the preparation of the cleanser composition of the present invention. Those wherein the content of the derivative (5) is 3% by weight or below are preferable. Alternatively, the solutions which can be used for the preparation of the cleanser composition of the present invention include those wherein the content of the derivative (5) is 5% by weight or below based on the solid content (weight) of the solution. Those wherein the content of the derivative (5) is 3% by weight or below are still more preferable. As described, however, it is most desirable to use solutions which are substantially free from the derivative (5) as the one containing the component (B). When a solution containing the component (B) is one containing a large amount of the glycerol derivative (5), the resulting cleanser composition will be very poor in lathering property unfavorably. Further, although the above solution containing the component (B) may also contain impurities other than the glycerol derivative (5), for example, inorganic salts such as sodium chloride, it is preferable to use a solution containing such impurities in a small content.

Further, it is preferable to use, as the solution containing the component (B), the one having a solid content of 20% by weight or above.

The cleanser composition of the present invention generally contains the component (B) in an amount of 0.5 to 40% by weight, preferably 1 to 20% by weight, still more preferably 3 to 15% by weight, based on the total weight of the composition. When the amount of the component (B) is too small, the feeling of the skin cleansed will not be good when the cleanser composition is used in hard water, because calcium salt of the phosphate type surfactant is formed.

In the cleanser composition of the present invention, the weight ratio of the component (A) to the component (B), i.e., (A)/(B), is not particularly limited, but the ratio is generally from 99/1 to 1/99, preferably from 97/3 to 20/80, still more preferably from 95/5 to 60/40.

When the cleanser composition of the present invention comprises the above components (A') and (B') as the essential components, the weight ratio of the component (A') to the component (B') is preferably from 75/25 to 98/2, still more preferably from 85/15 to 95/5.

According to the prior art, when the phosphate type surfactant as the component (A) takes the form of a triethanolammonium salt or an alkali metal salt, there has been a problem that when the concentration of the salt in the solution becomes 30% by weight or above, rapid viscosity increase or gelation occurs to be difficult to handle. Therefore, when a phosphate type surfactant of the form of a salt of phosphric acid ester such as triethanolamine salt and an alkali metal salt was used in the preparation of a cleanser composition, its content could not be enhanced.

On the contrary, when the component (A) is used together with the component (B), a cleanser composition which is lowly irritant and exhibits high detergency and which exhibits a low viscosity even when it contains the salt of the phosphoric acid ester in a concentration of as high as 30% by weight or above can be obtained. When it is desired to enhance the content of the salt of the phosphoric acid ester, it is suitable to use, as the component (B), a compound represented by the formula (3-1) wherein p-a is 3 to 15 and/or a compound represented by the formula (3-2) wherein p-b is 3 to 15, or a mixture thereof with a compound represented by the formula (4-1) wherein q-a is 3 to 15 and/or a compound represented by the formula (4-2) wherein q-b is 3 to 15.

When the cleanser composition of the present invention contains the component (A) in an amount of 35% by weight or above, it is desirable that the cleanser composition further contains a polyhydric alcohol. Polyhydric alcohol includes ethylene glycol, diethylene glycol, propylene glycol, dipropylene glycol and so forth, among which propylene glycol, dipropylene glycol and ethylene glycol are preferable.

In the cleanser composition of the present invention, it is preferable that the weight ratio of the sum total of the components (A) and (B) to the polyhydric alcohol, i.e,. [(A)+(B)]/the polyhydric alcohol, is from 80/20 to 99/1. When this ratio is lower then 80/20, the cleanser composition to be obtained will be poor in lathering property and detergency, though the concentration of the component (A) in the composition can be enhanced. On the contrary, when the ratio exceeds 99/1, it will be impossible to prepare a solution containing the component (A) in a concentration of 35% by weight or above.

When the cleanser composition of the present invention comprises the above-mentioned components (A') and (B') as the essential components, it is preferable that the weight ratio of the sum total of the components (A') and (B') to the polyhydric alcohol is from 90/10 to 99/1.

The pH of the cleanser composition of the present invention is preferably 3 to 9, still more preferably 4 to 8 (the condition of the determination of pH; an aqueous solution having a surfactant content of 5% by weight is used), though it is not particularly limited.

The cleanser composition of the present invention may optionally contain a component(s) which is (are) conventionally used in cleanser compositions at need in addition to the above essential components, so long as the effects of the present invention are not impaired. Examples of such components include surfactants such as anionic surfactants other than the amide ether carboxylic acids or the phosphates, and nonionic surfactants, humectants such as propylene glycol and glycerol, viscosity modifiers such as methylcellulose, hydroxyethylcellulose, carboxyvinyl polymer, polyoxyethylene glycol distearate and ethanol, preservatives, antioxidants, pearling agents, ultraviolet absorbers, coloring matters and fragrances.

The cleanser composition of the present invention can be applied as cleansers of various objects such as those for tableware and clothes, in addition to those for the skin and the hair. It is preferable that the total surfactant content of the cleanser composition of the present invention, i.e., the total content of the components (A) and (B) and other surfactant (s), be 30% by weight or above when the composition has a solid form, 20% by weight or above when it has a pasty form, or 10% or above when it has a liquid form.

The cleanser composition of the present invention is lowly irritant to the skin, exhibits a high lathering property, gives creamy foam in quality, and can give an excellent feeling to the skin cleansed even when it is used in hard water, thus being particularly useful as a cleanser composition for the skin and the hair.

EXAMPLE

The present invention will now be described in more detail by referring to the following Examples, though the present invention is not limited to them. [Synthesis of a mixture of amide ether carboxylic acid with amide ether]

Synthesis Example 1

A mixture comprising 214.4 g (1 mol) of methyl laurate, 61.7 g (1.02 mol) of monoethanolamine and 15.3 g of a 30% by weight methanolic solution of sodium methoxide was heated at 90° C. under 50 mmHg for 5 hours. To the obtained reaction product, 88.2 g (2 mol) of ethylene oxide was introduced under the conditions of 100 to 110° C. and 0 to 3.5 atm (gauge).

331 g of the reaction mixture thus obtained was heated to 70 to 75° C. 174.8 g (1.5 mol) of sodium monochloroacetate (SMCA) and 65.2 g of solid sodium hydroxide were added thereto in 4 hours. The SMCA and the sodium hydroxide were each divided into five portions, which were added at the initiation of the reaction and after 1, 2, 3 and 4 hours from the initiation. After the completion of the addition of the whole amounts thereof, the resulting reaction mixture was maintained at that temperature for one hour.

Then, the temperature of the reaction mixture was raised to 85° C., followed by the addition of 5.3 g of water. The resulting mixture was maintained at that temperature for one hour to give 592 g of a reaction mixture. 500 g of water was added to the reaction mixture thus obtained and the temperature of the mixture was brought to 90° C. Then, a 36% aqueous solution of hydrochloric acid was added to the resulting mixture to adjust the pH of the mixture to 2.8. The reaction mixture was stirred for one hour and then allowed to stand for one hour to cause phase separation. 545 g of an acid-form product was obtained from the upper organic phase. A 30% aqueous solution of sodium hydroxide was added to the organic phase containing the acid-form product to adjust the pH thereof to 7, followed by the addition of water. Thus, an amide ether derivative mixture 1 shown in Table 1 was obtained as a transparent solution. Synthesis Example 2

By effecting the same procedure as that of the Synthesis Example 1, except that the amount of ethylene oxide used was changed, an amide ether derivative mixture 2 shown in the Table 1 was obtained.

TABLE 1

| Sample | Compd. (3-1) | Compd. (4-1) | Content in the solid components (wt. %) | | | | | |
|---|---|---|---|---|---|---|---|---|
| | | | (3-1) | (4-1) | (3-1) + (4-1) | (5) | others | (3-1):(4-1) |
| amide ether derivative mixture 1 | $R^4$: $C_{11}H_{23}$ $R^{5a}$: H M: Na k: 3 | $R^4$: $C_{11}H_{23}$ $R^{5a}$: H f: 3 | 82 | 14 | 96 | 0 | 4 | 85:15 |
| amide ether derivative mixture 1 | $R^4$: $C_{11}H_{23}$ $R^{5a}$: H M: Na k: 5 | $R^4$: $C_{11}H_{23}$ $R^{5a}$: H f: 5 | 77 | 18 | 95 | 0 | 5 | 81:19 |

*: sodium chloride, glycolates, etc.

Examples 1 and 2

Cleanser compositions each having the composition specified in Table 2 were prepared.

In the Table 2, the component (A) indicates the concentration of the surfactant as the active component, while the component (B) indicates the concentration as the solid matter. The pH of each cleanser composition was adjusted with an aqueous solution of sodium hydroxide and/or citric acid. The balance is composed of water.

Each cleanser composition was evaluated for the quantity of the formed foams, quality of foam, feeling of the skin after cleansing and irritations to the skin according to the following methods, and the results are given in the Table 2.

Quantity of the Formed Foams and Quality of Foam

The quantity of the formed foams and quality of foam were evaluated by twenty expert panelists by the method which comprises taking 1 g of each cleanser composition on the hand and lathering it with water of 15° DH.

With respect to the quantity of the formed foams, score 4 refers to excellent foaming, score 3 good foaming, score 2 slightly poor foaming and score 1 poor foaming, and in the Table 2, the case wherein the average of the scores of the twenty panelists is 3.5 to 4.0 is shown by "⊚", the case wherein the average of the scores is 2.5 to 3.4 by "○", the case wherein the average of the scores is 1.5 to 2.4 by "Δ", and the case wherein the average of the scores is 1.0 to 1.4 by "x".

With respect to the quality of foam, score 4 refers to creamy and very smooth foam, score 3 creamy and smooth foam, score 2 slightly coarse and slightly poorly smooth foam and score 1 coarse and poorly smooth foam, and in the Table 2, the case wherein the average of the scores of the twenty panelists is 3.5 to 4.0 is shown by "⊚", the case wherein the average of the scores is 2.5 to 3.4 by "○", the case wherein the average of the scores is 1.5 to 2.4 by "Δ", and the case wherein the average of the scores is 1.0 to 1.4 by "x".

Feeling of the Skin after Cleansing

In the feeling of the skin after cleansing, the hands were rinsed after the above evaluations of the quantity of the formed foams and quality of foam and dried to evaluate the feeling of the dried skin.

Score 4 refers to smooth moist skin, score 3 smooth and somewhat moist skin, score 2 somewhat dry skin and score 1 dry skin, and in the Table 2, the case wherein the average of the scores of the twenty panelists is 3.5 to 4.0 is shown by "⊚", the case wherein the average of the scores is 2.5 to 3.4 by "○", the case wherein the average of the scores is 1.5 to 2.4 by "Δ", and the case wherein the average of the scores is 1.0 to 1.4 by "x".

Irritations to the Skin

With respect to the irritations to the skin, each cleanser composition was applied to the normal skin of five guinea pigs each four times and the reaction of the skin after four-times application was evaluated according to the following criteria.

Namely, score 5 refers to no irritation (no reaction), score 4 slight irritation (slight erythema), score 3 weak irritation (clear erythema), score 2 medium irritation (clear erythema accompanied with edema) and score 1 strong irritation (clear erythema accompanied with necrosis or apparent death), and in the Table 2, the case wherein the average of the scores of the twenty panelists is 3.5 to 5.0 is shown by "○", the case wherein the average of the scores is 2.5 to 3.4 by "Δ" and the case wherein the average of the scores is 1.0 to 2.4 by "x".

TABLE 2

| | | Ex. | | Comp. Ex. | | |
|---|---|---|---|---|---|---|
| | | 1 | 2 | 1 | 2 | 3 |
| Component (A) | K salt of lauryl phosphate/ K salt of dilauryl phosphate (monolauryl/dilauryl = 95/5) | 10 | — | 10 | — | — |
| | K salt of lauryl phosphate/ K salt of dilauryl phosphate (monolauryl/dilauryl = 75/23) | — | 10 | — | — | 10 |
| Component (B) | sodium mono(lauramidopoly-oxyethylene(3.0))acetate | 5 | 6 | — | 7 | — |
| | lauramidopolyoxyethylene(3.0) ether | — | 2 | — | — | 4 |
| | pH | 7.2 | 7.0 | 7.1 | 6.8 | 7.0 |

TABLE 2-continued

| | | Ex. | | Comp. Ex. | | |
|---|---|---|---|---|---|---|
| | | 1 | 2 | 1 | 2 | 3 |
| Evaluation | quantity of the formed foams | ○ | ⊚ | Δ | x | x |
| | quality of foam | ○ | ⊚ | Δ | Δ | x |
| | feeling of the skin after cleansing | ⊚ | ⊚ | Δ | Δ | x |
| | irritations to the skin | ○ | ○ | ○ | ○ | ○ |

Example 3

A shampoo having the composition which will be described below and a pH of 7.5 was prepared. This shampoo was found to be lowly irritant to the skin and excellent in lathering property and quality of foam.

Formulation

| | (% by wt.) |
|---|---|
| 1. amide ether derivative mixture 1 | 4 |
| 2. K salt of lauryl phosphate/ K salt of dilauryl phosphate (monolauryl/dilauryl = 95/5) | 14 |
| 3. lauric diethanolamide | 3 |
| 4. citric acid | an appropriate amount |
| 5. NaOH | an appropriate amount |
| 6. fragrance | 0.2 |
| 7. deionized water | the balance |

Example 4

A body shampoo having the composition which will be described below and a pH of 6.9 was prepared. This shampoo was found to be lowly irritant to the skin and excellent in lathering property, quality of foam, and the feeling of the skin after the cleansing and drying.

Formulation

| | (% by wt.) |
|---|---|
| 1. amide ether derivative mixture 2 | 5 |
| 2. Na salt of lauryl phosphate/ Na salt of dilauryl phosphate (monolauryl/dilauryl = 95/5) | 10 |
| 3. laurylamine oxide | 4 |
| 4. citric acid | an appropriate amount |
| 5. NaOH | an appropriate amount |
| 6. fragrance | 0.2 |
| 7. deionized water | the balance |

Example 5

A body shampoo having the composition which will be described below and a pH of 7.5 was prepared. This shampoo was found to be lowly irritant to the skin and excellent in lathering property, quality of foam and the feeling of the skin after the cleansing and drying.

Formulation

|  | (% by wt.) |
|---|---|
| 1. Sodium mono(lauramidopolyoxy-ethylene(3.0) acetate | 3 |
| 2. lauramidopolyoxyethylene(3.0) ether | 5 |
| 3. triethanolamine salt of lauryl phosphate/triethanolamine salt of dilauryl phosphate (monolauryl/dilauryl = 95/5) | 10 |
| 4. sodium salt of polyoxyethylene(3) lauryl ether sulfate | 5 |
| 5. citric acid | an appropriate amount |
| 6. NaOH | an appropriate amount |
| 7. fragrance | 0.2 |
| 8. deionized water | the balance |

We claim:

1. A cleanser composition comprising the following components (A) and (B):

3 to 15% by weight of component (A): a phosphate type surfactant (1) represented by the following formula (1), or a mixture of the phosphate type surfactant (1) and a phosphate type surfactant (2) represented by the following formula (2), wherein the weight ratio of the phosphate type surfactant (1) to the phosphate type surfactant (2) is from 100/0 to 70/30:

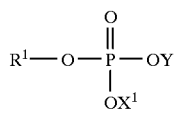
(1)

wherein $R^1$ represents a linear or branched alkyl or alkenyl group having 6 to 24 carbon atoms, and $X^1$ and Y each represents a hydrogen atom, an alkali metal atom, ½ (alkaline earth metal atom), an ammonium group, an alkanolammonium group or a group consisting of one hydrogen atom and a basic amino acid, and

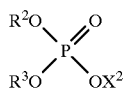
(2)

wherein $R^2$ and $R^3$ each represents a linear or branched alkyl or alkenyl group having 6 to 24 carbon atoms, and $X^2$ represents a hydrogen atom, an alkali metal atom, ½(alkaline earth metal atom), an ammonium group, an alkanolammonium group or a group consisting of one hydrogen atom and a basic amino acid; and 3 to 15% by weight of component (B): at least one amide ether carboxylic acid represented by the following formula (3-2)

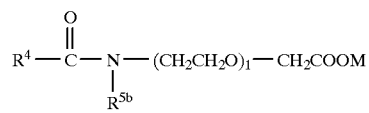
(3-2)

wherein M represents a hydrogen atom, an alkali metal atom, ½ (alkaline earth metal atom), an ammonium group, an alkanolammonium group or a group consisting of one hydrogen atom and a basic amino acid, $R^4$ represents a linear or branched alkyl or alkenyl group having 5 to 23 carbon atoms or a phenyl group which may be substituted with a linear or branched alkyl or alkenyl group having 5 to 23 carbon atoms, $R^{5b}$ represents $—(CH_2CH_2O)_m—CH_2COOM$, wherein M is as defined above, or $—(CH_2CH_2O)_n—$H, 1; m and n are each a number of 1 or more; and $(1+x(m)+y(n))$, wherein x and y are each a number of 0 to 1 and satisfy the relationship of $x+y=1$ when x and y are each a number of 0 to 1 and satisfy the relationship of $x+y=1$.

2. A cleanser composition comprising the following components (A) and (B):

3 to 15% by weight of component (A): a phosphate type surfactant (1) represented by the following formula (1), or a mixture of the phosphate type surfactant (1) and a phosphate type surfactant (2) represented by the following formula (2), wherein the weight ratio of the phosphate type surfactant (1) to the phosphate type surfactant (2) is from 100/0 to 70/30:

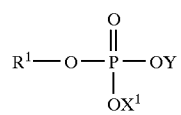
(1)

wherein $R^1$ represents a linear or branched alkyl or alkenyl group having 6 to 24 carbon atoms, and $X^1$ and Y each represents a hydrogen atom, an alkali metal atom, ½ (alkaline earth metal atom), an ammonium group, an alkanolammonium group or a group consisting of one hydrogen atom and a basic amino acid, and

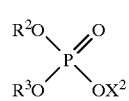
(2)

wherein $R^2$ and $R^3$ each represents a linear or branched alkyl or alkenyl group having 6 to 24 carbon atoms, and $X^2$ represents a hydrogen atom, an alkali metal atom, ½(alkaline earth metal atom), an ammonium group, an alkanolammonium group or a group consisting of one hydrogen atom and a basic amino acid; and 3 to 15% by weight of component (B): at least one amide ether carboxylic acid represented by the following formula (3-1)

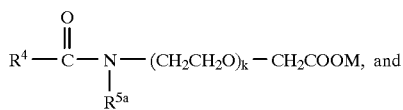   (3-1)

wherein M represents a hydrogen atom, an alkali metal atom, ½(alkaline earth metal atom), an ammonium group, an alkanolammonium group or a group consisting of one hydrogen atom and a basic amino acid, $R^4$ represents a linear or branched alkyl or alkenyl group having 5 to 23 carbon atoms or a phenyl group which may be substituted with a linear or branched alkyl or alkenyl group having 5 to 23 carbon atoms, $R^{5a}$ represents a hydrogen atom or an alkyl group having 1 to 3 carbon atoms, and k is a number of 1 to 20.

3. The cleanser composition as set forth in claim 1, which further comprises a glycerol derivative (5) represented by the following formula (5) in an amount of at most 5% by weight based on the sum total weight of the component (B) and the glycerol derivative (5):

   (5)

wherein $R^6$ represents $-(CH_2CH_2O)_{r-1}-CH_2COOM$, wherein M is as defined above, or $-(CH_2CH_2O)_{s-1}-H$, $R^7$ represents $-(CH_2CH_2O)_{r-2}-CH_2COOM$, wherein M is as defined above, or $-(CH_2CH_2O)_{s-2}-H$, $R^8$ represents $-(CH_2CH_2O)_{r-3}-CH_2COOM$, wherein M is as defined above, or $-(CH_2CH_2O)_{s-3}-H$, r-1, s-1, r-2, s-2, r-3 and s-3 are each 0 or a positive number and z, which is defined as $\{x_1(r-1)+y_1(s-1)\}+\{x_2(r-2)+y_2(s-2)+\{x_3(r-3)+y_3(s-3)\}$, wherein $x_1$ and $y_1$ are each a number of 0 to 1 and satisfying the relationship of $x_1+y_1=1$, $x_2$ and $y_2$ are each a number of 0 to 1 and satisfying the relationship of $x_2+y_2=1$, and $x_3$ and $y_3$ are each a number of 0 to 1 and satisfying the relationship of $x_3+y_3=1$, is a number of 0 to 57.

4. The cleanser composition as set forth in claim 1, which further comprises a polyhydric alcohol.

5. The cleanser composition as set forth in claim 4, wherein the weight ratio of the sum total of the components (A) and (B) to the polyhydric alcohol is from 80/20 to 99/1.

6. The cleanser composition as set forth in claim 1, wherein $R^1$, $R^2$ and $R^3$ each represents a linear or branched alkyl or alkenyl group having 8 to 18 carbon atoms, $X^1$, $X^2$ and Y each represents a hydrogen atom, an alkali metal atom, a triethanolammonium group or an ammonium group, $R^4$ represents a linear or branched alkyl or alkenyl group having 8 to 18 carbon atoms, M represents a hydrogen atom, an alkali metal atom, a triethanolammonium group or an ammonium group.

7. The cleanser composition as set forth in claim 6, wherein $X^1$, $X^2$, Y and M are each an alkali metal atom.

8. The cleanser composition as set forth in claim 6, which further comprises a polyhydric alcohol.

9. The cleanser composition as set forth in claim 6, which further comprises a polyhydric alcohol, wherein the weight ratio of the sum total of the components (A) and (B) to the polyhydric alcohol is from 90/10 to 99/1.

10. The cleanser composition as set forth in claim 2 wherein R5a represents a hydrogen atom and k is a number of 3 to 15.

* * * * *